(12) United States Patent
Nishida

(10) Patent No.: US 7,934,928 B2
(45) Date of Patent: May 3, 2011

(54) IMPLANTER

(75) Inventor: Tetsuya Nishida, Shinjuku-ku (JP)

(73) Assignee: Nihon University, Tokyo (JP)

( * ) Notice: Subject to any disclaimer, the term of this patent is extended or adjusted under 35 U.S.C. 154(b) by 246 days.

(21) Appl. No.: 12/161,423

(22) PCT Filed: Jan. 17, 2007

(86) PCT No.: PCT/JP2007/050609
§ 371 (c)(1),
(2), (4) Date: Aug. 27, 2008

(87) PCT Pub. No.: WO2007/083670
PCT Pub. Date: Jul. 26, 2007

(65) Prior Publication Data
US 2009/0061386 A1    Mar. 5, 2009

(30) Foreign Application Priority Data
Jan. 20, 2006  (JP) .................................. 2006-012530

(51) Int. Cl.
*A61C 8/00* (2006.01)
*A61F 2/02* (2006.01)

(52) U.S. Cl. ....................... 433/173; 433/176; 623/17.17
(58) Field of Classification Search .......... 433/172–176; 623/17.17
See application file for complete search history.

(56) References Cited

U.S. PATENT DOCUMENTS

| | | | |
|---|---|---|---|
| 4,081,908 A * | 4/1978 | Sneer | 433/176 |
| 4,531,916 A | 7/1985 | Scantlebury et al. | |
| 5,123,844 A | 6/1992 | Wakai et al. | |
| 6,213,774 B1 | 4/2001 | Lazarof | |
| 6,394,807 B2 * | 5/2002 | Robinson | 433/173 |
| 2005/0282113 A1 | 12/2005 | Fraiman | |

OTHER PUBLICATIONS

International Search Report, International Application No. PCT/JP2007-050609 Dated Mar. 29, 2007.
Form IB/338—Notification of Transmittal of Translation of the International Preliminary Report on Patentability dated Sep. 18, 2008 from the corresponding International Application No. PCT/JP2007/050609.
Translation of the International Preliminary Report on Patentability.

* cited by examiner

*Primary Examiner* — John J Wilson
(74) *Attorney, Agent, or Firm* — Young Basile

(57) ABSTRACT

An implanter is provided, which enables rebuilding of an interdental papilla with a simple method. An implanter 1 is made up of a T-shaped steel member as a main body. The lateral side portions centering a web portion 2 in a flange portion 3 are inclined so as to be closer to the web portion 2 with respect to a plane perpendicular to the web portion 2, to provide an angular shape, with its peak residing in a portion joining with the web portion. A plurality of holes 4 large enough for gingival fibers to thrust in are opened in the flange portion 3. One or more embedding portions 5 are projected from a tip end portion (lower end portion) of the web portion 2. Each of the embedding portions 5 has a tip end portion with at least an acute shape, or a shape that enables embedding by being driven into alveolar bone 10.

2 Claims, 4 Drawing Sheets

IMPLANTER

TECHNICAL FIELD

The present invention relates to an implanter used for rebuilding interdental papilla in the oral cavity.

BACKGROUND ART

In implant therapy, artificial tooth roots made of titanium for replacing natural tooth root, are embedded in the alveolar bone so as to be located at the positions where the teeth used to be present, for example, being extracted. Then, after the artificial tooth roots have been cured for several months until being fitted to the bone, artificial teeth are made and attached to the artificial tooth root.

The alveolar bone after the loss of teeth is relatively liable to dissolve and thus the gum is liable to degenerate. Accordingly, the interdental papilla between the artificial tooth roots tends to lower. Further, the interdental papilla between the teeth affected by periodontal disease, for example, may disappear.

The lowering of the interdental papilla may form an excessive interdental space to raise the following problems of:

(1) Aesthetically bad-looking appearance;
(2) Phonetically tending to cause unclear lisp sound; and
(3) Hygienically unfavorable tendency of causing food debris to stick between teeth.

Possible measures that can be considered for these problems in the conventional art, may have been to make the artificial teeth in a slightly larger size to narrow the space between the artificial teeth, or to rebuild the interdental papilla between the artificial teeth, using the guided bone regeneration technique or transplantation technique.

DISCLOSURE OF THE INVENTION

The method for narrowing the space between artificial teeth by making large artificial teeth, has a limitation in the degree of narrowing the space, from the viewpoint of the balance in the shapes with other teeth. Moreover, this method is not purposed to rebuild the interdental papilla.

Under existing circumstances, formation using the guided bone regeneration technique or transplantation technique takes time and presents difficulty in successfully achieving rebuilding of the bone at an interdental papilla portion.

In addition, there has been provided no such an implanter, so far, as to be used for rebuilding interdental papilla.

The present invention has been made focusing on the matters provided above, and has as its object to provide an implanter which is able to rebuild interdental papilla with a simple method.

In order to solve the problems provided above, an invention among the present inventions, an implanter which is attached in order to rebuild an interdental papilla between teeth, characterized in that the implanter comprises: embedding portion to be embedded in alveolar bone residing in an interdental papilla portion; and an implanter body which is embedded in gingiva and projected from the alveolar hone, being integrated with the embedding portions, and that the implanter comprises: an upright portion which extends in a direction intersecting the widthwise direction of the interdental space and in a direction moving away from the embedding portion; and a roof portion which laterally extends from an upper end portion of the upright portion along the widthwise direction of the interdental space, and has an angular shape as viewed from a direction perpendicular to the widthwise direction of the interdental space.

The implanter characterized in that a plurality of holes are opened in a surface of the implanter body for enabling gingival fibers to thrust therein.

DESCRIPTION OF SYMBOLS

1 Implanter
1A Implanter body
2 Web portion (upright portion)
3 Flange portion (roof portion)
4 Holes
5 Embedding portion
10 Alveolar bone
11 Gum
12 Artificial tooth root

BEST MODE FOR CARRYING OUT THE INVENTION

With reference to the drawings, hereinafter will be described an embodiment of the present invention.
(Configuration)

Figure 1:
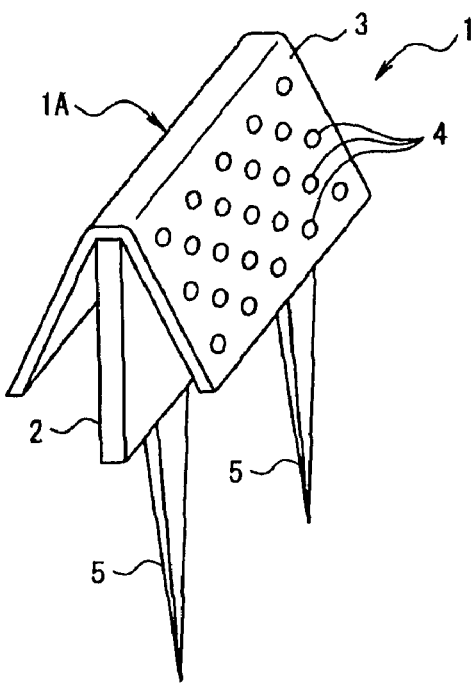
FIG. 1 is a perspective view showing an implanter related to an embodiment based on the present invention.

FIG. 1 is a schematic diagram showing an implanter of the present embodiment.

To explain the configuration first, an implanter 1 of the present embodiment is constituted by processing, as a main body, a T-shaped steel member having a thickness of 0.3 mm to 1 mm. In the T-shaped steel member, a web portion 2 serves as an upright portion and a flange portion 3 serves as a roof portion. The T-shaped steel member constitutes an implanter body 1A.

The lateral side portions centering the web portion 2 in the flange portion 3 are inclined so as to be closer to the web portion 2 with respect to the plane perpendicular to the web portion 2. Thus, the outline of the top surface as viewed from the front has an angular shape, with its peak residing in a portion joining with the web portion 2. It should be appreciated that each inclined plane does not necessarily have to lie on a straight line. Also, the state of the inclination may be adjusted using pliers, for example, at the time when or immediately after the attachment to the alveolar bone.

The flange portion 3 is provided with a plurality of openings forming holes 4 each having a size large enough for the gingival fibers to thrust in.

Further, one or more embedding portions 5 are projected from the tip end portion (lower end portion) of the web portion 2. From the viewpoint of preventing wobbling after attachment, the number of the embedding portions 5 may preferably be two or more. Also, the web portion 2 and the embedding portions 5 may be integrally molded. Each of the embedding portions 5 has a tip end portion with at least an acute shape, that is, a shape enabling embedding by being driven into the alveolar bone, and is applied with a surface treatment for joining with the bone.

At least one of the plurality of embedding portions 5 has a length equal to or larger than that of the web portion 2. Having such a length equal to or larger than that of the web portion 2, the implanter body 1A can be reliably set upright.

The implanter 1 (the implanter body 1A and the embedding portions 5) having the configuration described above is made of titanium. Further, at least the surface of the flange portion 3 in the implanter body 1A has a whitish color, being coated with apatite.

The width of the flange portion 3 (dimension along the widthwise direction of the interdental space) is set to 1.5 mm to 2.5 mm. Generally, the space between artificial tooth roots is regulated to be 3 mm or more. Also, when adults are concerned, the standard of the space between natural tooth roods is generally estimated as being about 3 mm as well. Thus, the width of the flange portion 3 constituting the roof portion is set to 2.5 mm or less to enable arrangement at an interdental papilla portion. The reason why the width is regarded as requiring 1.5 mm or more is that this width as a minimum is considered to be sufficient for rebuilding a natural appearance of the interdental papilla portion. As a matter of course, when the width is larger or smaller than the standard, the range provided above may be made larger or smaller.

Figure 2:
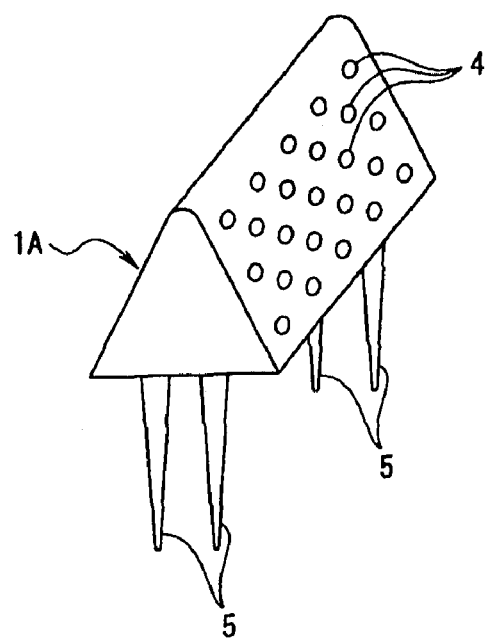
FIG. 2 is a drawing showing another example of the implanter related to the embodiment based on the present invention.

In this regard, the above embodiment exemplifies a case where the implanter 1 is constituted using the T-shaped steel member as a base, but the embodiment is not limited to this. Alternatively, for example, the implanter body 1A may be constituted so as to have a boxed shape with its top surface having an angular shape, as shown in FIG. 2.

(Examples of Use)

Hereinafter will be explained some examples of use of the implanter 1. The explanation hereinafter is given, assuming that the implanter is used in an implant surgery.

Figure 3A:
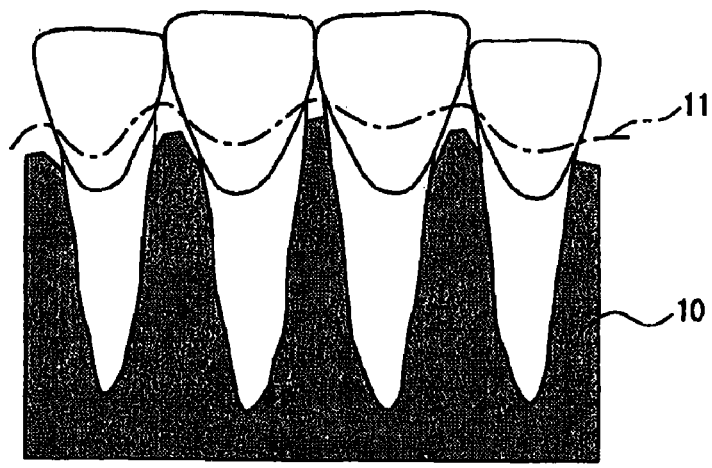
FIG. 3 is a drawing showing an example of a construction procedure.
Figure 3B:
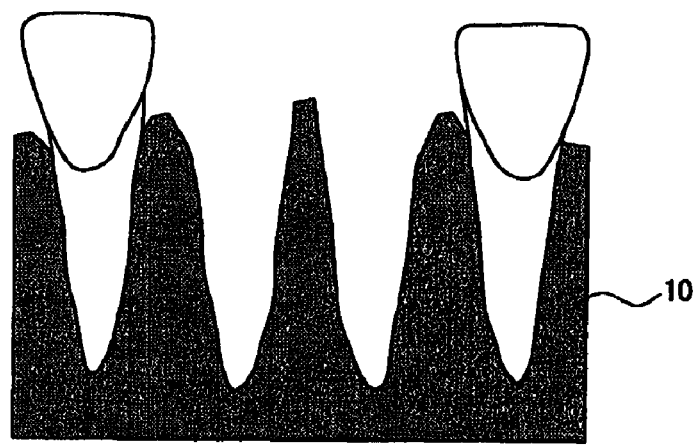
Figure 3C:
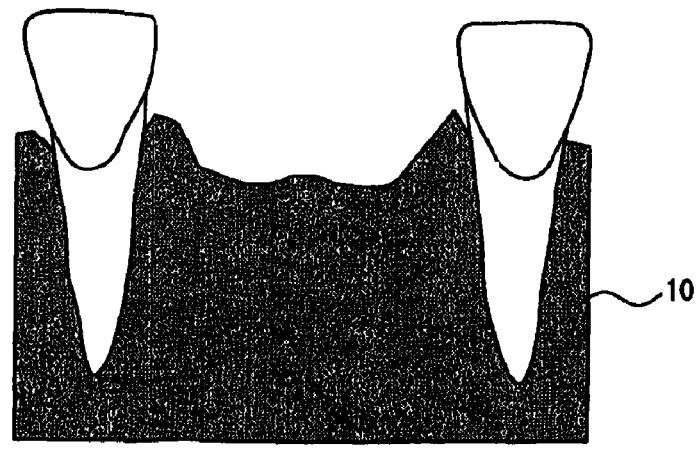

From the state shown in FIG. 3A, the natural tooth roots are extracted (see FIG. 3B) after effecting regional anesthesia. Then, the gingiva is incised to expose alveolar bone 10 (jawbone) in order to attach implants thereto. In this case, the gingiva of the interdental papilla portion is also incised to expose the alveolar bone 10 (see FIG. 3C). It should be noted that, in FIGS. 3, 5 and 6, the upper limit position of the gingiva (gum) is indicated by a dash-dot line 11.

Then, holes are opened for artificial tooth roots at the positions where artificial tooth roots 12 are to be embedded, using a special drill. The present embodiment exemplifies a case where two artificial tooth roots 12 are simultaneously implanted. However, there may be a case where one of them has already been embedded.

Figure 4:
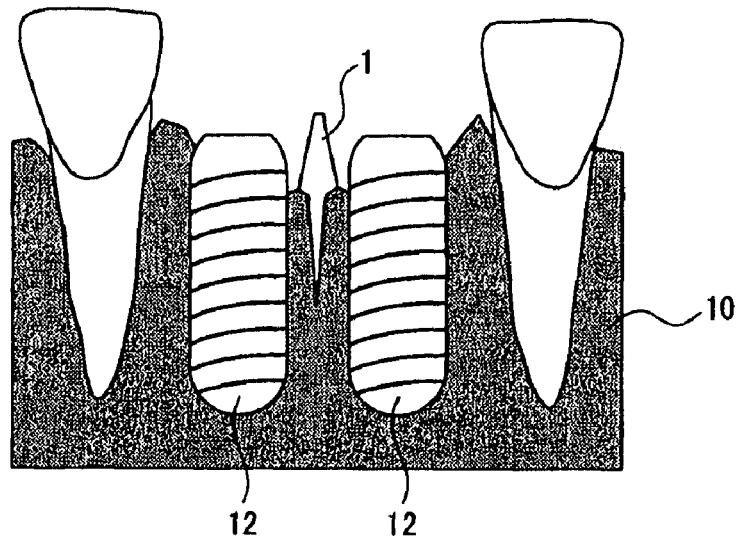
FIG. 4 is a drawing showing a state where an implanter is attached to alveolar bone.

Then, the artificial tooth roots 12 are embedded in the respective holes for artificial tooth roots (see FIG. 4). The embedding may be performed by screwing or driving.

Subsequently, shallow holes are opened using a chisel, for example, at the positions where the embedding portions 5 of the implanter 1 are to be driven on a surface of the alveolar bone 10 between the artificial tooth roots 12. In the state where the tip end portions of the embedding portions 5 are in contact with the respective shallow holes, the implanter 1 is driven to embed the embedding portions 5 into the alveolar bone 10 (see FIG. 4). In this case, setting is made so that the widthwise direction of the web portion 2 (the direction in which the embedding portions 5 are juxtaposed) will be perpendicular to the widthwise direction of the interdental space (or will be directed in the in-and-out direction of the oral cavity).

Also, a makeshift abutment is attached to the head of each embedded artificial tooth root 12, and at the same time the incised gingiva is stitched up at least to cover the implanter 1.

In this state, the artificial tooth roots 12 are cured for several months, for example, until the artificial tooth roots 12 fit to the bone 10. During the curing, the fibers of the gingiva covering the implanter 1 will thrust in the holes 4 of the flange portion 3 as well, which holes constitute the flange portion 3, to have the implanter 1 more reliably fitted to the gingiva.

The gum 11 is so thin that the surface color of the flange portion 3 may be highly likely to be seen through. However, the whitish surface color of the flange portion 3 can prevent the beauty from being spoiled.

After the artificial tooth roots 12 have joined with the bone, artificial teeth 13 are attached to the respective artificial tooth roots 12 (see FIG. 5), wherein the dental bite is adjusted at the same time. The description provided above has exemplified a case where the makeshift abutments are attached, with the top portions of the abutments being exposed from the gingiva. However, the artificial tooth roots 12 may be cured by also closing the gingiva on the upper side thereof, and when the curing is over, the gingiva may be incised into small pieces for the attachment of the artificial teeth 13.

Figure 5:
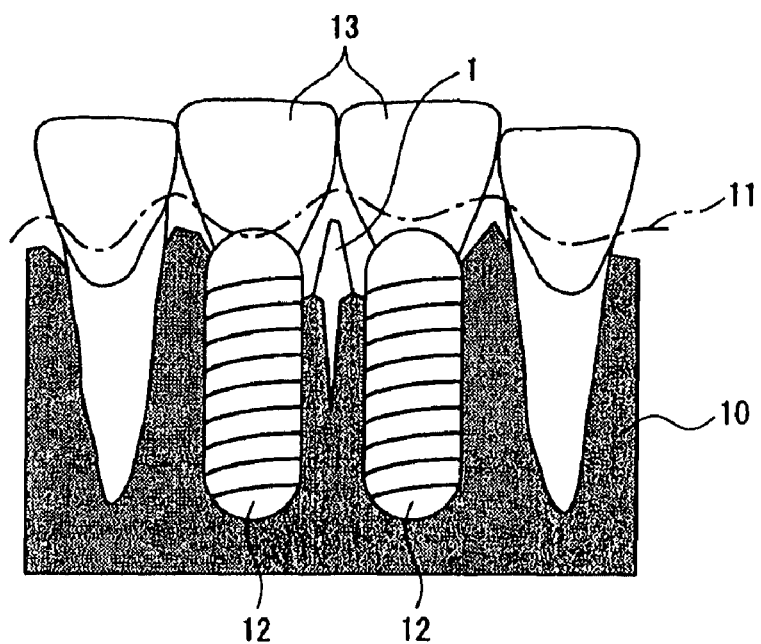
FIG. 5 is a drawings showing a state where the implanter is covered with gingiva.

Use of the implanter 1 as described above may enable rebuilding of the interdental papilla between the implants with a simple operation. There is a tendency that the alveolar bone 10 lying between the implants, in particular, dissolves and thus the position of the gum 11 steps back. However, as shown in FIG. 5, the interdental papilla can be readily rebuilt by embedding the implanter 1. Specifically, the appearance of something natural can be imparted to the gingiva (the gum 11 in particular).

Figure 6:
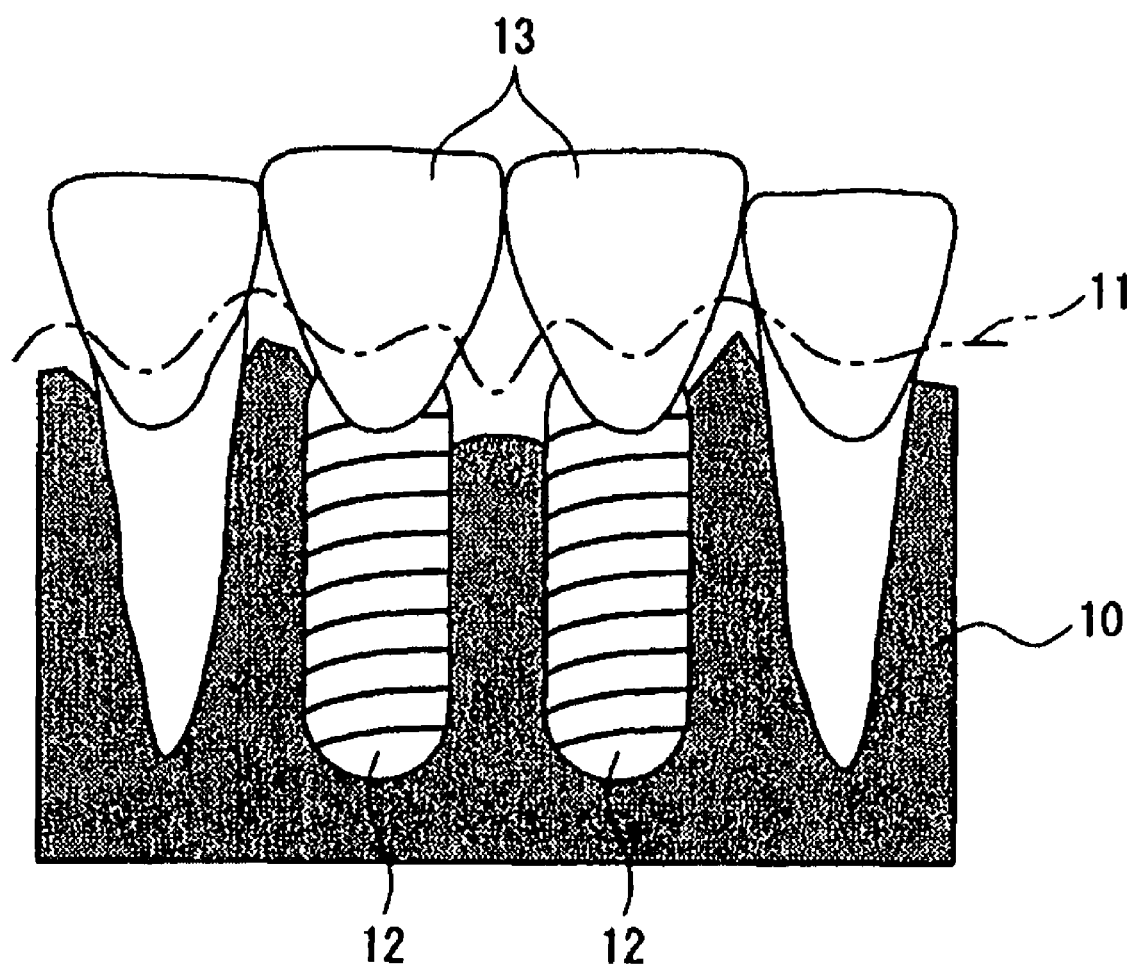
FIG. 6 is a drawing showing a case where there is no implanter.

It should be appreciated that, when the implanter 1 is not embedded, the gum 11 is degenerated between the implants, as shown in FIG. 6, to form a large space (commonly called "black triangle").

Thus, the adverse effect of the degeneration of the interdental papilla, as provided above in the explanation of the problems, can be eliminated.

Specifically:

(1) Aesthetically good-looking can be achieved by imparting the appearance of the gingiva with something natural;

(2) Lisp sound can be improved by eliminating or reducing the interdental space and thus by preventing breath from leaking out from between the teeth; and (3) Hygiene in the oral cavity can be improved by permitting food debris to hardly stick between the teeth.

The implanter 1 is particularly effective in rebuilding the interdental papilla between implants. However, even between natural tooth roots, the implanter 1 may be embedded at the position where the gum 11 has stepped back, to thereby rebuild the interdental papilla.

When only the embedding of the implanter 1 is considered, the implanter 1 may well be embedded by incising the gingiva, at a position on the side of the tongue (inner side in the oral cavity) rather than at a position on a tooth row.

INDUSTRIAL APPLICABILITY

According to the present invention, the interdental papilla can be rebuilt using a simple method.

The invention claimed is:

1. An implanter for embedding in an interdental space between teeth, the implanter comprising:

an embedding portion configured to be embedded in alveolar bone beneath an interdental papilla portion in the interdental space between two teeth, the interdental space having a width between the two teeth; and an implanter body integral with and extending from the embedding portion and configured to project above the alveolar bone, the implanter body having a surface in which holes are formed, the holes configured for receiving gingival fibers therein to embed the implanter body in gingival, wherein the implanter body comprises:

an upright portion which has a planar configuration with an upper end portion and a lower end portion, the embedding portion extending from the lower end portion, wherein the upright portion is configured to extend in a direction orthogonal to the width of the interdental space when embedded; and a roof portion having an apex at the upper end portion of the upright portion with side portions extending from the apex on both sides of the upright portion, the side portions configured to extend toward the teeth of the interdental space when embedded so as to have an angular shape as viewed from the direction orthogonal to the width of the interdental space, wherein the roof portion and the upright portion define a cavity on each side of the upright portion.

2. The implanter of claim 1, wherein the embedding portion comprises two or more tip end portions each with an acute shape configured to enable insertion of the embedding portion in the alveolar bone.

* * * * *